United States Patent

Körfer et al.

[11] Patent Number: 6,126,972
[45] Date of Patent: Oct. 3, 2000

[54] PROCESS FOR THE PREPARATION OF AQUEOUS SODIUM METHIONINATE SOLUTIONS AND USE OF THOSE SOLUTIONS IN THE PRODUCTION OF A GRANULATE

[75] Inventors: Martin Körfer, Johannesberg; Lutz Rohland, Offenbach; Wolfram Binder, Rodenbach; Hans Joachim Hasselbach, Gelnhausen; Hans Christian Alt, Gelnhausen-Meerholz; Klaus Huthmacher, Gelnhausen; Heidemarie Kniesel, Hosbach, all of Germany

[73] Assignee: Degussa-Huls AG, Germany

[21] Appl. No.: 09/309,278

[22] Filed: May 11, 1999

[30] Foreign Application Priority Data

May 16, 1998 [DE] Germany ............................ 198 22 099

[51] Int. Cl.$^7$ ............................ A23K 1/18; C07C 321/00
[52] U.S. Cl. ................................ 426/2; 426/807; 562/559
[58] Field of Search .......................... 426/2, 807; 562/559

[56] References Cited

U.S. PATENT DOCUMENTS

| | | | |
|---|---|---|---|
| 4,069,251 | 1/1978 | Mannsfeld et al. | 260/534 |
| 4,391,988 | 7/1983 | Spindler et al. | 562/559 |
| 4,705,689 | 11/1987 | Tanner et al. | 426/2 |

FOREIGN PATENT DOCUMENTS

| | | | |
|---|---|---|---|
| 197 07 380 A1 | 8/1998 | Germany | A23K 1/16 |
| WO 98/37772 | 9/1998 | Germany . | |

*Primary Examiner*—Gabrielle Brouillette
*Assistant Examiner*—Robert Madsen
*Attorney, Agent, or Firm*—Pillsbury Madison & Sutro LLP

[57] ABSTRACT

A process for the preparation of aqueous sodium methioninate solutions having a low sodium carbonate content from the crude hydrolysis mixtures obtained in the hydrolysis of 5-(β-methylmercaptoethyl)-hydantoin with from 1.1 to 6 equivalents of sodium hydroxide and/or sodium carbonate, by separating off sodium carbonate monohydrate while heating, and granulates subsequently prepared from those solutions by various processes.

16 Claims, No Drawings

PROCESS FOR THE PREPARATION OF AQUEOUS SODIUM METHIONINATE SOLUTIONS AND USE OF THOSE SOLUTIONS IN THE PRODUCTION OF A GRANULATE

CROSS-REFERENCE TO RELATED APPLICATION

This application claims priority from German Application No. 198 22 099.5, filed on May 16, 1998, the subject matter of which is hereby incorporated herein by reference.

BACKGROUND OF THE INVENTION

1. Field of the Invention

The invention relates to a process for the preparation of aqueous sodium methioninate solutions having a low sodium carbonate content from the crude hydrolysis mixtures obtained in the hydrolysis of 5-(β-methylmercaptoethyl)-hydantoin with from 1.1 to 6 equivalents of sodium hydroxide and/or sodium carbonate, by separating off sodium carbonate monohydrate while heating, and also relates to granulates subsequently prepared from those solutions by various processes.

2. Background Information

Methionine and aqueous solutions of methionine salts, especially of sodium methioninate (DE 31 05 009 C), but also synthetic substances such as the methionine-hydroxy analogue (MHA), are used worldwide as feed additives for rearing poultry, swine and other useful animals and are of benefit mainly to the production of animal protein.

According to requirements, solid or liquid forms are preferably employed.

The sodium methioninate solution that is available on the market has a concentration of 40 wt. % methionine and, in contrast to MHA, corresponds to solid methionine, when compared on an equimolar basis, as regards its biological valency. Several methods come into consideration for the preparation of such sodium methioninate solutions, for example 1. Dissolution of isolated methionine in sodium hydroxide solution.
2. Alkaline hydrolysis of 5-(β-methylmercaptoethyl)-hydantoin with NaOH and/or $Na_2CO_3$, or with a mixture of $NaOH/Na_2CO_3/NaHCO_3$.
3. Alkaline hydrolysis of methionine amide.

Although process 1 yields the purest form of product, it is, however, more expensive in comparison with production of the solid because it involves an additional process step, and it is, therefore, less economical than the preparation of methionine itself. Processes 2 and 3, on the other hand, start at an earlier stage in the preparation of methionine and hence achieve a relieving according to capacity of the solids portion of the DL-methionine preparation.

The preparation of 5-(β-methylmercaptoethyl)-hydantoin takes place in a known manner by direct synthesis from the usual starting materials methylmercaptopropionaldehyde (MMP) and hydrocyanic acid in the presence of ammonia and carbon dioxide. Methionine amide is prepared in a known manner by hydrolysis of methionine nitrile, which in turn is obtained by direct synthesis from the usual starting materials MMP, hydrocyanic acid or ammonium cyanide and ammonia.

The hydrolysis solutions obtained according to process 2 contain relatively large amounts of sodium carbonate, which must be separated off.

To that end, the hydrolysis mixture is concentrated according to DE-OS 31 04 997 to a sodium methioninate content of from 40 to 65 wt. % and is then cooled to room temperature or below, and the sodium carbonate decahydrate that then forms is separated off. However, it is frequently obtained in a form which can be filtered only with difficulty.

According to U.S. Pat. No. 4,931,987, the procedure is reversed. The sodium carbonate is first allowed to crystallise out, and then the resulting solutions are concentrated.

DE-OS 31 05 009 discloses a process in which methanol or ethanol is added before the separation.

Depending on special requirements, it can be expedient to use a solid or liquid form of the animal feed supplement. The decision regarding the form of administration is dependent, inter alia, on the available mixing tools and on the special preferences of each particular operator.

In the preparation of the mixed feed, the various feeds and additives are initially in the form of individual components which, according to their properties, are prepared, for example, by milling, coarse grinding, drying or purifying. If the individual components have the necessary properties, the actual mixing operation is carried out in a suitable mixing unit. The individual batches for mixing differ according to the size of the unit. In the supplementation of mixed feeds, the essential amino acid methionine is used in concentrations of the order of from 0.01 to 1.0 wt. %. Those amounts are added directly to the mixed feed by means of appropriate weighing and metering systems.

In DE-OS 31 05 009 it is described that aqueous solutions of sodium or potassium methioninate have the same methionine activity as solid methionine when used as a feed additive.

A methionine salt-based granulate is known from DE-197 07 380 of Feb. 15, 1997.

SUMMARY OF THE INVENTION

The object of the invention is to make available a process which, as desired, yields sodium methioninate solutions containing no or only a small amount of sodium carbonate and $NaHCO_3$, and the granulates which can be prepared therefrom.

The invention provides a process for the preparation of aqueous sodium methioninate solutions having a low sodium carbonate and $NaHCO_3$ content from the crude hydrolysis mixtures obtained in the hydrolysis of 5-(β-methylmercaptoethyl)-hydantoin with from 1.1 to 6 equivalents of sodium hydroxide and/or sodium carbonate, characterised in that water is distilled off from the crude hydrolysis mixture, preferably in two stages, especially after the addition of further sodium hydroxide, preferably to an excess of 1 mole/liter, based on the methioninate, until the sodium methioninate content is from 60 to 90 wt. %, and the resulting sodium carbonate or hydrogen carbonate is separated off at temperatures of from 90 to 140° C., especially from 110 to 130° C. Evaporation crystallisation has proved to be especially suitable as the crystallisation method.

The filtration properties are influenced in a very advantageous manner by the reduced viscosity of the solution in the hot state.

The filtrate subsequently has a residual sodium carbonate content of <6 wt. %, preferably ≦3.5 wt. %, especially <1.5 wt. %.

The solid, which consists of approximately 70 wt. % sodium carbonate and approximately 15 wt. % methionine and is generally separated off using a centrifuge or a decanter, is obtained according to the invention, in contrast to the prior art, at elevated temperature. It is then returned, without being cooled, to the hydantoin hydrolysis, which takes place at temperatures above 120° C. By means of this procedure, an economical closed-loop process for the preparation of the sodium methioninate solution can be produced.

If the residual content of sodium carbonate or hydrogen carbonate still present in the solution is undesired, it is reduced by the molar addition of free methionine corresponding to the sodium ion content. The methionine can be added either in the form of a solution or as a suspension. The final concentration of the product is optionally adjusted by the addition of water.

By heat treatment at temperatures of approximately from 80 to 200° C., especially from 130 to 170° C., with dwell times of from 0.1 to 3 hours, the carbonate can subsequently be decomposed, with removal of $CO_2$, and Na methioninate can be formed. For the specific removal of the $CO_2$ from the solution, an inert expulsion agent or water vapour is used. Where water vapour is used as the expulsion agent, it may either be supplied externally or be evaporated from the solution by means of suitable apparatuses such as, for example, falling film evaporators.

The removal of the $CO_2$ can be further assisted by the use of mechanical energy, for example in the form of stirring, or by the specific use of process-technological apparatuses which in particular promote the carrying out of chemical reactions with superimposed mass transfer from the liquid phase to the gas phase. There are suitable for that purpose, for example, countercurrent plate columns, packed columns, jet apparatuses or bubble columns.

According to that procedure, solutions of Na methioninate that are especially stable to storage are obtained. The invention also provides pourable granulates produced by shaping measures from the solutions so prepared containing no or only a small amount of sodium carbonate.

In an advantageous variant, the solution is concentrated further under atmospheric or reduced pressure, so that the removal of water from the solution occurs by means of pure evaporation, which is very favourable in terms of energy, and not by drying. At pressures of from 20 to 1000 mbar and temperatures of from 100 to 160° C., a solution or pseudomelt that is still free-flowing is obtained. The solution has residual water contents of only approximately from 0.5 to 3 wt. %. The pseudomelt has a solidification temperature of approximately from 40 to 80° C.

On account of those favourable marginal conditions, fluidised-bed granulation processes are especially suitable for producing granulates such as are employed in the field of application of the product.

The granulate has a bulk density of >650 kg/m$^3$, preferably >700 kg/m$^3$, with a particle size distribution of from 63 to 5000 μm, preferably from 100 to 3000 μm, especially from 100 to 1400 μm, with≈90% of the particles being present in a particle size of >100 μm.

The proportion of particles having a particle size <63 μm is generally not more than 2%, preferably 1%, and the dust content is 1%, preferably <0.5%.

An especially suitable granulating process for solutions having sodium methioninate contents of from >65 wt. % to 90 wt. % has three stages, a granulate production stage, a drying stage, and a product cooling stage.

The following applies in particular:

a) fluidised-bed build-up granulation is especially suitable for the granulation, b) drying may be carried out both in the fluidised bed and in, for example, a vacuum contact dryer, c) there are used for the cooling also, for example, a fluidised bed, a cooling coil or a cooling trough.

There is used as the drying gas pre-dried, heated air or nitrogen; the dew point of the gas is approximately from −10 to 40° C. Production of the granulate takes place by spraying the highly concentrated product solution directly into the fluidised bed. The atomising unit may be, other than is customary in the art, a two-component nozzle operated as a pressure nozzle. The formation of droplets is carried out by the spontaneous pressure drop at the nozzle head; the enveloping air can expediently be reduced in comparison with the usual method of operation (weight ratio solution:air approximately 2:1) to a markedly lower value of from 7:1 to 10:1. The enveloping air serves to introduce the droplets into the fluidised bed.

The air conditions in conjunction with the moisture content of the product in the fluidised bed are particularly important with regard to the temperature control of the apparatus. The particle size of the granulates can be carried out (sic) substantially via the production and the introduction of granulate seeds by means of crushing tools built into the fluidised bed internally, for example a pinned disk mill, or by external milling, for example, of oversize particles from the fluidised bed.

The drying step may follow on directly from the granulation in the same apparatus. Independent temperature control must be possible by means of suitable separating elements both at the supply to the drying stage and on the product side. The fine grains, or abraded material, discharged with the drying gas can likewise be returned to the granulation stage. The temperature in the drying stage is likewise dependent on the moisture content of the drying gas and of the granulate and is in the range of from 80 to 120° C.

When cooling to generally from 30 to 60° C. it must be ensured that the product is moved mechanically in a dry atmosphere and is kept dry until it has cooled, in order to prevent the grains from sticking together. For that reason, fluidised-bed coolers or cooling coils or cooling troughs are to be regarded as very suitable apparatuses. It is also possible to use other mechanically gentle apparatuses, for example cooling troughs, plate coolers or cooling coils. Those apparatuses are at least to be covered with a layer of dry gas in order to avoid sticking together of the product.

It is possible to carry out the entire fluidised-bed build-up granulation process not only continuously but also batchwise in only a single chamber of a fluidised bed. In that case, build-up granulation, drying and cooling are carried out in succession by means of appropriate temperature control.

As an alternative to the described granulate production process using fluidised-bed build-up granulation, it is also possible to produce the granulates by atomisation using two-component or flat jet nozzles, or by means of a droplet-forming process. In that case, the very highly concentrated solution or pseudomelt having a residual moisture content of from 0.5 to 10 wt. % is pressed at temperatures of from 70° C. (sic), preferably from 120 to 160° C., through a perforated plate having fine holes. By causing the plate to vibrate axially it is possible to obtain an especially uniform droplet spectrum even with that highly viscous solution. According to the invention, the droplets are allowed to solidify in a precipitation column in a dry inert gas, for example air or nitrogen.

The solidification is carried out at slightly elevated temperatures, so that further evaporation of water takes place at the same time. Finally, the pellets are collected in a fluidised bed and dried under the conditions described above. The granulate pellets so obtained are distinguished by especially good pourability, a uniform particle spectrum and a low dust content.

Another variant consists in producing the granulate by extruding the pseudomelt of the highly concentrated solution in an extruder with specific temperature control. In that process, an extrudate can be produced directly without further additives. According to the moulds used, granulates having a diameter of approximately from 500 to 5000 $\mu$m can be produced. Finally, if desired and necessary, the product can likewise be dried.

In order to improve the handling of the granulates to be produced, it is advisable to atomise and granulate the methionine salt solutions in the presence of silicate-based additives.

These include hydrophilic and hydrophobic silicas, of pyrogenic nature or prepared by precipitation of from 5 to 300 $m^3$/g, preferably spray-dried silicas. Finely divided zeolites, for example of type A or bentonite, may also be used.

The additives can either be suspended in the solution to be atomised or, preferably, be metered together with the stream of air into the apparatus in which the solution is atomised and, optionally, granulated.

The amount of other additives is from 0.1 to 10 wt. %, preferably from 0.1 to 5 wt. %, based on the granulated solid. Those additives include, in addition to the silicate-like compounds, substances which are by their nature preferred and are permitted in the feeds sector, especially fatty acids and their salts, preferably alkali or alkaline earth metal salts.

The fatty acids include especially stearic acid and palmitic acid or mixtures of fatty acids containing from 16 to 18 carbon atoms or their above-mentioned salts.

While sodium methioninate that has not been granulated readily forms clumps and loses its pourability on account of its hygroscopic behaviour, the same is, unexpectedly, not found with the granulates according to the invention. They remain pourable and easy to handle even when exposed to the weather.

DETAILED DESCRIPTION OF THE INVENTION

EXAMPLES

Example 1

There are used 1000 g of a solution obtained by dissolving 200 g of methionine and an equimolar amount of NaOH in 666 g of water, with the addition of 80 g of $Na_2CO_3$. While stirring, an amount of 600 g of water is removed from the solution by distillation, and the precipitate that forms is separated off in a screen-type centrifuge at temperatures >100° C. The filtrate contains 71% Na methioninate and only 1.1% $Na_2CO_3$, $NaHCO_3$; calculated as $Na_2CO_3$.

Example 2

There are used 1000 g of a crude hydrolysis mixture which has been prepared by hydrolysis of an aqueous solution of 5-($\beta$-methylmercaptoethyl)-hydantoin with a 2.5 molar equivalent aqueous $Na^+$ solution as a mixture of NaOH, $Na_2CO_3$ and $NaHCO_3$ at from 160 to 180° C. with removal of $CO_2$ and $NH_3$ from the reaction mixture, and which contains, for example, 231 g of Na methioninate and 84 g of a mixture of $Na_2CO_3$ and $NaHCO_3$, calculated as $Na_2CO_3$. 550 g of water are distilled off from that crude hydrolysis mixture, and the precipitate that forms is separated off at boiling temperatures of 127° C. over a heated pressure filter. The filtrate contains 60% Na methioninate and 5.4% of a mixture of $Na_2CO_3$, $NaHCO_3$; calculated as $Na_2CO_3$.

Example 3

Example 1 is repeated with the difference that the concentration by evaporation is carried out in two stages. In the first stage, 350 g of water are distilled off, the suspension is then stirred for a time in that state, and then a further 200 g of water are distilled off. The precipitate is again separated off at boiling temperatures of 127° C. over a heated pressure filter. The filtrate contains 62% sodium methioninate and only 3.2% $Na_2CO_3$, $NaHCO_3$; calculated as $Na_2CO_3$.

Example 4

Example 2 is repeated with the difference that 250 g of water are distilled off in the second stage. In this case the boiling temperature is 131° C., the filtrate contains 71% sodium methioninate and only 3.5% $Na_2CO_3$ $NaHCO_3$; calculated as $Na_2CO_3$.

Example 5

There are used 1000 g of solution as obtained as the filtrate according to Example 3, and the solution is injected at a temperature of from 85 to 130° C. into a fluidised bed of granulate which has already been dried.

The droplets of the solution are distributed as a thin layer on the granulate which is already in place, and are dried by 6 $Nm^3$ of $N_2$, the nitrogen in the apparatus used cooling from 95° C. to 58° C. and the dew point of the gas rising from 8° C. to 35° C. The residual moisture content of the granulate is 6.4%.

Example 6

Example 4 is repeated with the difference that the drying gas is dehumidified to a dew point of, for example, -2° C. before it enters the fluidised bed. With 15 $Nm^3$ of $N_2$, the granulate has a residual moisture content of only 2.4%.

What is claimed is:

1. In a process for the preparation of aqueous sodium methioninate solutions having a low sodium carbonate content from the crude hydrolysis mixtures obtained in the hydrolysis of 5-($\beta$-methylmercaptoethyl)-hydantoin with from 1.1 to 6 equivalents of sodium hydroxide and/or sodium carbonate, the improvement comprising the steps of:
   (i) distilling off water from the crude hydrolysis mixture until the sodium methioninate content is from 60 to 90 wt. %, and
   (ii) separating off the resulting sodium carbonate in anhydrous form as the monohydrate and/or hydrogen carbonate containing sodium methioninate residues, at a temperature of from 90 to 140° C., to obtain an aqueous sodium methioninate solution.

2. The process according to claim 1, wherein, further sodium hydroxide is added to the crude hydrolysis mixture prior to step (i).

3. The process according to claim 1, wherein the sodium carbonate containing sodium methioninate residues that has been separated off is recycled, without being cooled, and returned to the crude hydrolysis mixture.

4. The process according to claim 1, wherein after the sodium carbonate monohydrate has been separated off, free methionine is added to the aqueous sodium methioninate solution in an amount that is approximately the molar equivalent of the amount of residual sodium carbonate, the solution is heated to from 80 to 200° C., optionally under pressure, and $CO_2$ that forms is removed from the solution.

5. The process according to claim 4, wherein water vapour or an inert gas is used for removing the $CO_2$.

6. The process according to claim 4, wherein the aqueous sodium methioninate solution is stirred to remove $CO_2$.

7. The process according to claim 1, wherein the aqueous sodium methioninate solution is then converted into a pourable granulate.

8. The process according to claim 7, wherein the aqueous sodium methioninate solution is converted into pourable granulate using fluidised-bed granulation.

9. The process according to claim 8, wherein the aqueous sodium methioninate solution is concentrated at temperatures of from 100 to 160° C. and pressures of from 10 to 1000 mbar to a residual water content of from 0.5 to 3 wt. % prior to fluidised-bed granulation.

10. The process according to claim 9, wherein an aqueous sodium methioninate solution containing from 80 to 99.5 wt. % of sodium methioninate is extruded and the extrudate is then optionally dried.

11. The process according to claim 10, wherein the aqueous sodium methioninate solution contains from 93 to 99.5 wt. % of sodium methioninate.

12. The process according to claim 7, wherein the aqueous sodium methioninate solution is converted using build-up fluidised-bed granulation.

13. The process according to claim 12, wherein the aqueous sodium methioninate solution contains from >65 wt. % to 95 wt. % sodium methioninate.

14. The process according to claim 12, wherein the granulation process is divided into the following three stages a) production of the granulate;

b) drying of the granulate; and cooling of the granulate.

15. The process according to claim 12, wherein the weight ratio of aqueous sodium methioninate solution:air is from 7:1 to 10:1.

16. The process according to claim 12, wherein sodium methioninate having a residual moisture content of from 0.5 to 10 wt. % is (a) pressed at from 70 to 160° C. through a perforated plate having fine holes and the plate is optionally made to vibrate axially to form droplets or (b) atomised and the resulting granulate is then optionally dried.

* * * * *